United States Patent [19]

Chin

[11] Patent Number: 4,476,866
[45] Date of Patent: Oct. 16, 1984

[54] COMBINED LARGE AND SMALL BORE SYRINGE

[75] Inventor: Albert K. Chin, San Francisco, Calif.

[73] Assignee: Thomas J. Fogarty, Palo Alto, Calif.

[21] Appl. No.: 406,030

[22] Filed: Aug. 6, 1982

[51] Int. Cl.³ .................................... A61M 29/02
[52] U.S. Cl. ................................ 128/344; 604/90; 604/271
[58] Field of Search ............... 128/344, 348.1; 604/90, 604/56, 191, 199, 271, 159, 208, 211, 184, 231, 203, 218

[56] References Cited

U.S. PATENT DOCUMENTS

| | | | |
|---|---|---|---|
| 984,037 | 2/1911 | Sheets | 604/191 |
| 1,234,582 | 7/1917 | Trueblood | 604/191 |
| 2,515,956 | 7/1950 | Greenberg | 604/218 |
| 2,869,543 | 1/1959 | Ratcliff et al. | 604/90 |
| 3,326,215 | 6/1967 | Sarnoff et al. | 604/90 |
| 3,343,539 | 9/1967 | Moorhouse | 604/211 |
| 3,370,754 | 2/1968 | Cook et al. | 604/90 |
| 3,685,514 | 8/1972 | Cheney | 604/90 |
| 3,749,084 | 7/1973 | Cucchiara | 604/191 |
| 4,188,949 | 2/1980 | Antoshkiw | 604/199 |
| 4,254,774 | 3/1981 | Boretos | 128/344 |
| 4,271,839 | 6/1981 | Fogarty et al. | 128/344 |
| 4,332,254 | 6/1982 | Lundquist | 128/344 |

Primary Examiner—Dalton L. Truluck
Assistant Examiner—Gene B. Kartchner
Attorney, Agent, or Firm—Limbach, Limbach & Sutton

[57] ABSTRACT

In a combined large and small bore syringe, the small bore syringe is used as the plunger for the large bore syringe. Movement of the small bore syringe plunger produces a high pressure, low volume flow while subsequent movement of the entirety of the small bore syringe as the plunger of the large bore syringe produces a low pressure, high volume liquid flow.

8 Claims, 3 Drawing Figures

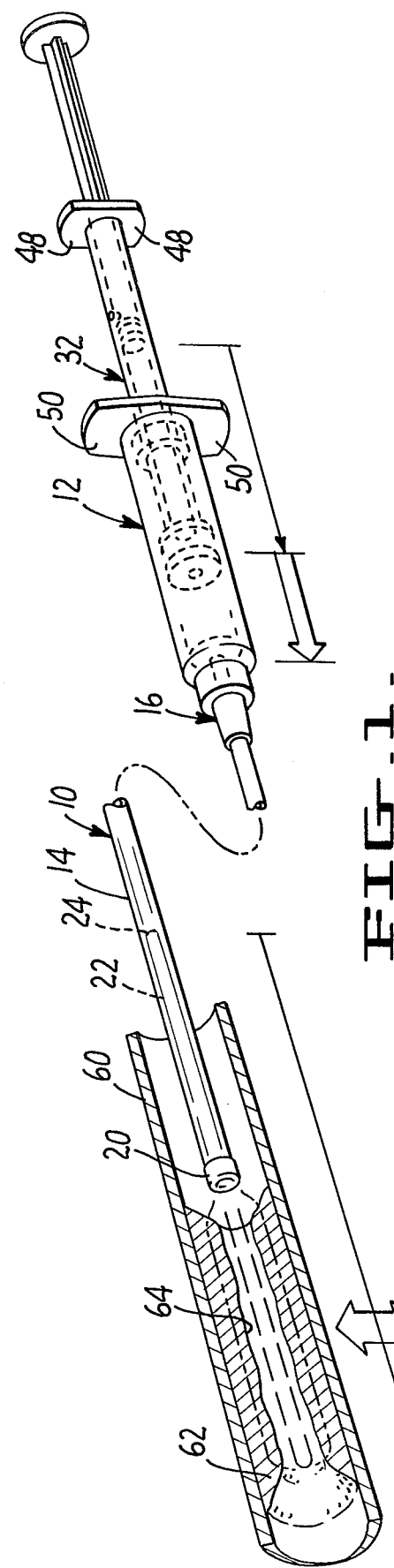
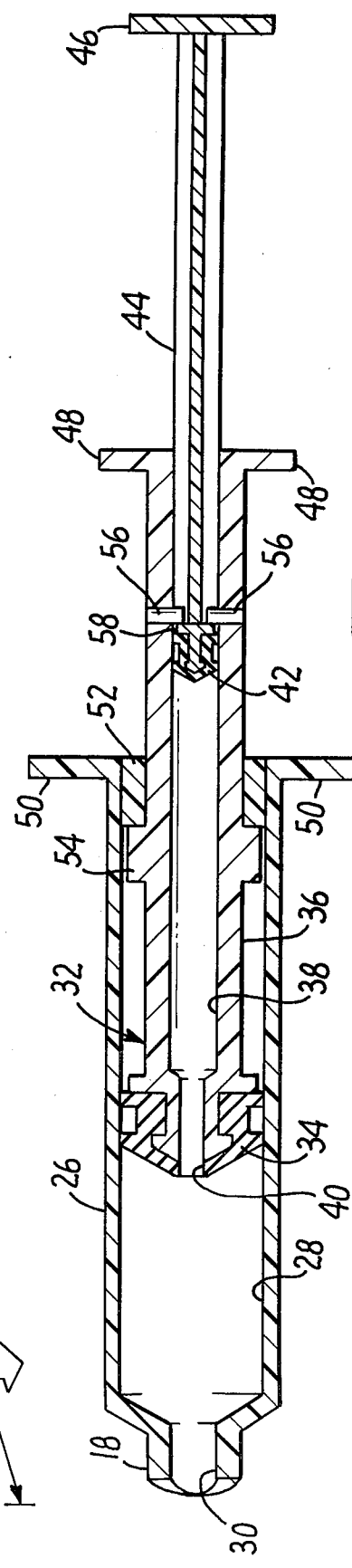
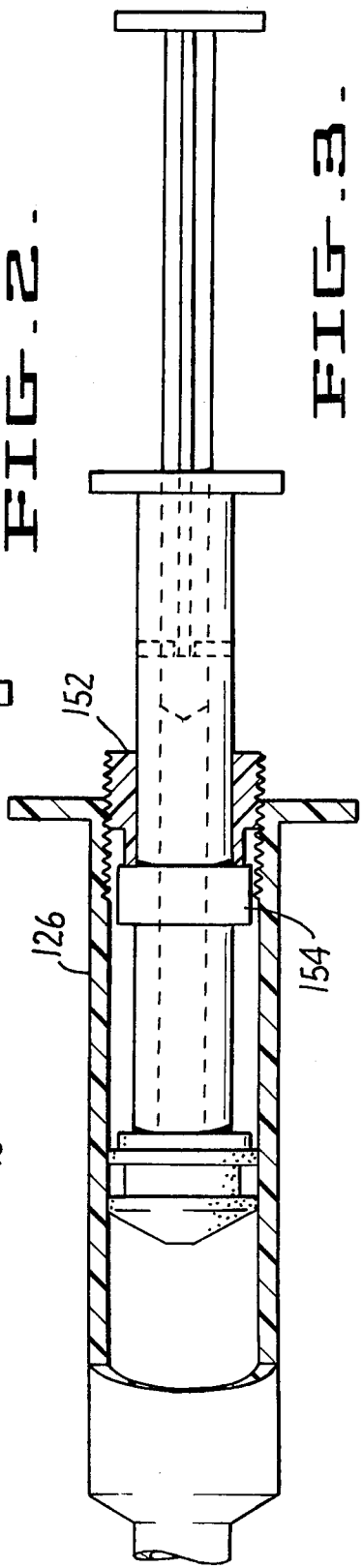

COMBINED LARGE AND SMALL BORE SYRINGE

BACKGROUND OF THE INVENTION

(1) Field of the Invention

The field of the invention is in the broad sense medical syringes. More specifically, the invention relates to dilatation catheters of the inversion-eversion type and a plunger-type actuator therefor characterized by a small bore stage adapted to provide an initial high fluid pressure to evert the balloon element of the catheter and a subsequent lower pressure, higher volume condition to inflate the balloon element.

(2) Description of the Prior Art

I am not aware of any combined large and small bore syringe suitable for catheter actuation, as described above, or for other purposes requiring an initial high pressure, low volume condition followed by a low pressure, high volume condition.

I am aware of the following prior art which disclose a variety of concentric dual plunger syringes: U.S. Pat. Nos. 2,869,543; 2,929,459; 3,326,215; 3,685,514; 4,128,009; 4,188,949; 4,254,768; 4,273,257.

In the foregoing patents, the plungers are of substantially the same diameter, and the purpose of the dual syringe arrangement is either to mix two different fluids during the course of injection or to maintain the fluids in separate condition.

SUMMARY OF THE INVENTION

The gist of the invention is the provision in an invert-evert dilatation catheter of actuator means comprising a first stage to evert the balloon element under high pressure, low volume conditions and a second stage to inflate the balloon element under low pressure, high volume conditions. The inclusion of such a first stage in the actuator means enables the catheter balloon to be everted under safe manually applied pressures which are well within the range of capabilities of everyone.

DESCRIPTION OF THE DRAWING

FIG. 1 is a view in perspective of the syringe-catheter of the invention.

FIG. 2 is an enlarged view in diametral section of the syringe portion of the apparatus of FIG. 1.

FIG. 3 is a sectional-elevational view of a further embodiment of the syringe portion of the apparatus.

DESCRIPTION OF THE PREFERRED EMBODIMENT

The device of the invention is comprised of a dilatation catheter portion indicated generally at 10 and a syringe portion indicated generally at 12.

The catheter portion 10 is comprised of an elongated flexible tube 14 having its proximal end attached by fitting means 16 to the open distal end 18 of syringe portion 12. Sleeved over and fixedly attached to the distal end of tube 14 is the proximal end 20 of an elongated balloon element 22 having a closed distal end 24. The balloon element is made of a non-elastomeric plastic material such as thin vinyl tubing.

The syringe portion 12 comprises a housing 26 having defined therein a cylindrical passageway 28 terminating in an outlet passage 30 of reduced size, the latter being in communication with the catheter tube 14. A piston member 32 comprised of flexible land 34 and cylindrical tube 36 is slidably disposed within cylinder 26. Tube 36 is provided with passageway 38 which communicates with a smaller outlet passageway 40, the latter in turn communicating with passageways 28 and 30. Slidably disposed within passageway 38 is a piston element comprising land 42 and rod 44 to which the land is fixedly attached. The rod 44 is provided with a typical cruciform cross-section which terminates at its proximal end in a pusher disc 46.

Preferably, the bore of passageway or cylinder 28 has a cross-sectional area which is a plurality of times as great as the cross-sectional area of the bore of passageway or cylinder 38. In addition, preferably the distal outlet end of large bore cylinder 28 has a cross-sectional area which is a plurality of times as great as the cross-sectional area of the distal outlet end of small bore cylinder 38.

The inner cylindrical element 32 is provided at its proximal end with finger tabs 48 and the outer cylindrical member 26 is provided with finger tabs 50. The cylindrical elements 26 and 32 are provided with ring elements 52 and 54 which interengage to limit the suction stroke of the piston element 32 and retain the latter within the cylinder 26. Element 32 is provided with inwardly directed retainer pins 56 which engage behind piston rod flange 58 to limit the suction stroke of the inner piston 42 within element 32 and prevent disconnection therebetween.

The catheter syringe is shown in condition for operation in FIG. 1. The catheter portion is positioned within an artery 60 adjacent a section of arteriosclerotic material 62. The balloon element 22 is inverted within tube 14. The tube 14 is otherwise filled with a liquid which also fills passageways 28, 30, 38 and 40.

The user places index and third fingers under the tabs 50 and thumb on the disc 46. This causes the piston 42 to move within the passageway 38 to cause a high pressure, low volume flow into catheter tube 14. Such flow imparts a high eversion force to the inverted balloon element 22, very readily and easily causing the balloon element to evert and extend within the lumen 64 of the arteriosclerotic material 62. The large bore syringe comprising land 34 and passageway 28 remains stationary and inactive until the piston 42 reaches the distal end of passageway 38. Continued conjoint movement thereafter of the piston rod 44 and cylinder element 32 causes a high volume, low pressure flow of liquid into the tube 14 to radially expand the balloon element and thereby dilate the arteriosclerotic material 62. Such low pressure, high volume flow may continue until the land 34 engages the distal end of passageway 28.

If the passageway 40 were to be plugged and the effort made to evert the balloon element from its starting position of FIG. 1 with the use only of the large bore syringe, a very high physical exertion would be required, involving the use of both hands on the part of weaker persons, to cause the balloon to evert. With the combined small bore and large bore syringe, the eversion of the balloon element may be accomplished with one hand very readily and comfortably even by a weaker person. It requires a high starting force to initiate inversion movement of the balloon element. This is accomplished by high pressure flow through passageway 40 under the influence of the low force-requiring movement of the small piston 42 within the small bore 38. Once everted, the radial expansion of the balloon element requires only low pressure, high volume flow which is provided by the movement of the large piston 34 within the large bore 28.

An additional feature of the device arises out of the presence of the two stop element systems 52, 54 and 56, 58. These prevent the plungers of the large and small bore syringes from being pulled out of their respective barrels 26 and 32. This allows both barrels of the syringe to be filled with one motion, i.e. by a pulling back on the plunger of the small bore syringe while holding the barrel of the large bore syringe fixed. Injection of a constant predetermined amount of liquid may be accomplished by situating the retaining rings or pins in a particular position along the barrels of the large and small bore syringes.

The embodiment of FIG. 3 is provided with a threaded retaining ring 152 which engages a matching threaded section of outer barrel 126. This allows for adjustment of the total injection volume of the syringe.

It is desirable to provide, in connection with the balloon dilatation catheter embodiment of the invention, a pressure relief valve, not shown, in the catheter-syringe system. This can very simply be comprised of a spring loaded ball relief valve within a small housing which may be mounted on the proximal end of tube 14 in communication with the interior thereof. Such a relief valve will insure that the pressure being applied to the material 62 will not reach a damaging level insofar as the artery 60 is concerned.

The combined large and small bore syringe may be used without the dilatation catheter to flush clogged venous lines. With venous lines, large initial pressures are needed to clear the obstructions in the lines and large volumes are needed to flush the lines after they have been opened.

What is claimed is:

1. In combination, a dilatation catheter comprising a catheter portion and a syringe portion having its distal outlet end attached to the proximal inlet end of the catheter portion, said catheter portion comprising an elongated flexible tube having an invertible-eversible balloon element attached to and received within the distal end thereof, said syringe portion comprising a large bore cylinder and a large bore piston fitted therein and a small bore cylinder and a small bore piston fitted therein, said large bore cylinder having a distal outlet end in communication with said flexible tube, said large bore piston having said small bore cylinder formed therein, said small bore cylinder having a distal outlet end in communication with said large bore cylinder, the cross-sectional area of the bore of said large bore cylinder being a plurality of times as great as the cross-sectional area of the bore of said small bore cylinder whereby compression of said small bore piston within said small bore cylinder functions to evert the balloon element under high pressure and compression of said large bore piston within said large bore cylinder functions to inflate the balloon element under a lower pressure for dilatation.

2. The combination of claim 1, the distal outlet end of said large bore cylinder having a cross-sectional area which is a plurality of times as great as the cross-sectional area of the distal outlet end of said small bore cylinder.

3. The combination of claim 1, including interengageable stop means carried by said large bore piston and by said large bore cylinder to define a predetermined liquid volume for said large cylinder and to prevent said large piston from being pulled out of said large cylinder, and interengageable stop means carried by said small bore piston and by said small bore cylinder to define a predetermined liquid volume for said small cylinder and to prevent said small piston from being pulled out of said small cylinder.

4. The combination of claim 3, said first-mentioned interengageable stop means being selectively adjustable relative to each other to variably control the total injection volume of said syringe portion.

5. A method of everting and inflating an invertible-eversible balloon element of a dilatation catheter comprising the following steps:
providing a syringe which includes a large bore cylinder and a large bore piston fitted therein, with said large bore cylinder having a distal outlet, and a small bore cylinder with a small bore piston fitted therein and having a distal outlet in communication with said large bore cylinder, said large bore piston having said small bore cylinder formed therein;
coupling said distal outlet of said large bore cylinder to an inlet of the dilating catheter;
disposing a fluid in the catheter and in said large and small bore cylinders of said syringe;
forcing said small bore piston into said small bore cylinder so as to cause a first volume of said fluid to be delivered to the catheter at a relatively high fluid pressure to evert the balloon element; and
forcing said large bore piston into said large bore cylinder so as to cause a second volume of said fluid to be delivered to the catheter at a relatively low fluid pressure to inflate the balloon for dilata-purposes.

6. A dilatation catheter comprising:
a catheter portion which includes an elongated flexible tube having an invertible-eversible balloon element attached to and received within the distal end thereof; and
a syringe portion which includes a relatively large bore cylinder and a large bore piston fitted therein, and a relatively small bore cylinder and a small bore piston fitted therein, said large bore cylinder having a distal outlet in communication with the proximal end of said flexible tube and said small bore cylinder having a distal outlet in communication with said large bore cylinder whereby compression of said small bore piston within said small bore cylinder functions to evert the balloon element under high pressure and compression of said large bore piston within said large bore cylinder functions to inflate the balloon element under a lower pressure for dilatation.

7. The dilation catheter of claim 6 wherein said small bore cylinder is formed in said large bore piston.

8. The dilation catheter of claim 7 wherein the cross-sectional area of the bore of said large bore cylinder is a plurality of times as great as the cross-sectional area of the bore of said small bore cylinder.

* * * * *